(12) United States Patent
You et al.

(10) Patent No.: US 9,662,646 B2
(45) Date of Patent: May 30, 2017

(54) ALDEHYDE ADSORBENT, METHOD FOR REMOVING ALDEHYDE, METHOD FOR PRODUCING ACETIC ACID, AND METHOD FOR REGENERATING ALDEHYDE ADSORBENT

(71) Applicant: CHIYODA CORPORATION, Yokohama-shi, Kanagawa (JP)

(72) Inventors: Zhixiong You, Yokohama (JP); Yoichi Umehara, Yokohama (JP); Tetsuro Matsumura, Yokohama (JP); Takeshi Minami, Yokohama (JP)

(73) Assignee: CHIYODA CORPORATION, Yokohama-shi, Kanagawa (JP)

( * ) Notice: Subject to any disclaimer, the term of this patent is extended or adjusted under 35 U.S.C. 154(b) by 0 days.

(21) Appl. No.: 14/897,125

(22) PCT Filed: Jun. 3, 2014

(86) PCT No.: PCT/JP2014/002950
§ 371 (c)(1),
(2) Date: Dec. 9, 2015

(87) PCT Pub. No.: WO2014/199593
PCT Pub. Date: Dec. 18, 2014

(65) Prior Publication Data
US 2016/0121320 A1 May 5, 2016

(30) Foreign Application Priority Data

Jun. 12, 2013 (JP) ................................. 2013-123746

(51) Int. Cl.
*B01J 39/20* (2006.01)
*C07C 51/44* (2006.01)
*C07C 51/47* (2006.01)
*C07C 45/79* (2006.01)
*C07C 51/12* (2006.01)
*B01J 39/05* (2017.01)
*B01J 39/19* (2017.01)
*B01J 49/06* (2017.01)
*B01J 49/53* (2017.01)

(52) U.S. Cl.
CPC ............... *B01J 39/20* (2013.01); *B01J 39/05* (2017.01); *B01J 39/19* (2017.01); *B01J 49/06* (2017.01); *B01J 49/53* (2017.01); *C07C 45/79* (2013.01); *C07C 51/12* (2013.01); *C07C 51/44* (2013.01); *C07C 51/47* (2013.01)

(58) Field of Classification Search
CPC ........ B01J 39/20; B01J 39/043; B01J 39/185; B01J 49/0008; B01J 49/0069; C07C 51/44; C07C 51/47; C07C 45/79; C07C 51/12
USPC .......................................................... 521/32
See application file for complete search history.

(56) References Cited

U.S. PATENT DOCUMENTS 5,969,175 A * 10/1999 Murao ................... C07C 253/34
558/411

FOREIGN PATENT DOCUMENTS

| EP | 487284 A2 | * | 5/1992 | ............ C07C 51/12 |
|---|---|---|---|---|
| JP | 3-262532 | | 11/1991 | |
| JP | 4-266843 A | | 9/1992 | |
| JP | 04266843 A | * | 9/1992 | |
| JP | 10-7638 A | | 1/1998 | |
| JP | 10007638 A | * | 1/1998 | |
| JP | 2006-10390 A | | 1/2006 | |
| JP | 2006-96764 A | | 4/2006 | |
| JP | 2007-218788 A | | 8/2007 | |
| JP | 2007218788 A | * | 8/2007 | |
| JP | 2007-284404 A | | 11/2007 | |

OTHER PUBLICATIONS

International Search Report dated Aug. 26, 2014, issued in counterpart application No. PCT/JP2014/002950 (2 pages).
Notification of Transmittal of Translation of the International Preliminary Report on Patentability dated Dec. 25, 2015, Form PCT/IB/338, Form PCT/IB/373 and Form PCT/ISA/237, issued in International Application No. PCT/JP2014/002950, with English translation. (7 pages).

* cited by examiner

*Primary Examiner* — Michael M Bernshteyn
(74) *Attorney, Agent, or Firm* — Westerman, Hattori, Daniels & Adrian, LLP

(57) ABSTRACT

An aldehyde adsorbent that can adsorb and remove aldehyde from a carboxylic acid-containing liquid is provided. The aldehyde adsorbent is an aldehyde adsorbent for adsorbing aldehyde in a carboxylic acid-containing liquid containing aldehyde, including a cation exchange resin ion-exchanged with a polyvalent amine in 1 to 99% by mol of the total exchange capacity.

8 Claims, 2 Drawing Sheets

ALDEHYDE ADSORBENT, METHOD FOR REMOVING ALDEHYDE, METHOD FOR PRODUCING ACETIC ACID, AND METHOD FOR REGENERATING ALDEHYDE ADSORBENT

TECHNICAL FIELD

The present invention relates to an aldehyde adsorbent, a method for removing aldehyde, a method for producing acetic acid and a method for regenerating an aldehyde adsorbent, which can allow aldehyde in a carboxylic acid-containing liquid containing aldehyde to be adsorbed and removed.

BACKGROUND ART

Acetic acid is a basic chemical having a wide range of applications such as raw materials for polyvinyl acetate, acetylcellulose and acetic acid esters, as well as solvents for terephthalic acid production plants. As a method for producing acetic acid, a so-called Monsanto's method (or a methanol carbonylation method) is known in which methanol is carbonylated by carbon monoxide in the presence of a rhodium catalyst or the like to produce acetic acid.

In the production of acetic acid by the carbonylation of methanol, a trace amount of acetaldehyde is by-produced. In addition, it is known that when low boiling components useful for the carbonylation reaction of methanol, such as methyl acetate and methyl iodide, are tried to be recovered, and returned to a carbonylation reaction step of methanol to be effectively reused, acetaldehyde is accumulated in the system. Acetaldehyde causes a condensation reaction under the carbonylation condition and is converted into unsaturated aldehydes having a high boiling point. These unsaturated aldehydes are precipitated in the lower portion of a distillation column or the like to cause the problem of blockage or the like, along with further progress of condensation. In addition, crotonaldehyde or the like has a boiling point close to that of acetic acid, and thus is difficult to be separated in a purification step of acetic acid and is incorporated into an acetic acid product, resulting in the deterioration in quality of acetic acid particularly as a reducing substance.

As the method for removing acetaldehyde accumulated in the system, PTL 1 discloses a method in which a mixed liquid of acetaldehyde, methyl acetate, acetic acid, methyl iodide and water is distilled using a distillation column having 40 steps or more in a reflux ratio of 10 or more to separate and remove acetaldehyde. In addition, PTL 2 discloses a method in which vapors of methyl iodide (boiling point: 42.4° C.), methyl acetate (boiling point: 56.9° C.) and acetaldehyde (boiling point: 20.2° C.) are brought into contact with water to thereby remove acetaldehyde by taking advantage that acetaldehyde has a low boiling point and is soluble in water.

The method in PTL 1, however, has the following problems: the distillation column for separating and removing acetaldehyde is provided with a complicated apparatus; and an expensive material that can correspond to hydroiodic acid produced by hydrolysis of methyl iodide is required to be used to result in the increase in apparatus cost.

In addition, the method of bringing the vapors into contact with water for absorption in PTL 2 has the following problem: methyl iodide and methyl acetate that are useful substances while being present in a small amount are dissolved in water and discharged together with acetaldehyde outside of the system.

It is to be noted that such problems occur with respect to not only acetaldehyde included in an acetic acid-containing liquid but also aldehydes included in various carboxylic acid-containing liquids.

Herein, PTL 3 shows a recovery method by an adsorption method. PTL 3 relates to a method for purifying nitrile, and discloses a method for bringing nitrile into contact with a cation exchange resin, on which a polyvalent amine is supported, to remove aldehyde in nitrile. This method, however, allows other carbonyl compounds that react with an amino group (for example, carboxylic acids and ketones) to be also simultaneously removed together with aldehyde, as described in paragraph [0011] in PTL 3, and therefore a problem of the method is that when used for removing aldehyde in a carboxylic acid-containing liquid, it causes the reduction in yield of carboxylic acid to thereby achieve no desired effects.

CITATION LIST

Patent Literature

PTL 1: Japanese Patent Application Laid-Open No. 2006-96764

PTL 2: Japanese Patent Application Laid-Open No. 2007-284404

PTL 3: Japanese Patent Application Laid-Open No. H10-7638

SUMMARY OF INVENTION

Technical Problem

In view of these problems, an object of the present invention is to provide an aldehyde adsorbent, a method for removing aldehyde, a method for producing acetic acid and a method for regenerating an aldehyde adsorbent, which can allow aldehyde to be adsorbed and removed from a carboxylic acid-containing liquid.

Solution to Problem

The present inventors have made intensive studies, and as a result, have found that an aldehyde adsorbent including a cation exchange resin ion-exchanged with a polyvalent amine in 1 to 99% by mol of the total exchange capacity can achieve the above object, thereby completing the present invention.

The aldehyde adsorbent according to the present invention is an aldehyde adsorbent for adsorbing aldehyde in a carboxylic acid-containing liquid containing aldehyde, including a cation exchange resin ion-exchanged with a polyvalent amine in 1 to 99% by mol of the total exchange capacity.

The amount ion-exchanged with the polyvalent amine is preferably 10 to 90% by mol and further preferably 40 to 80% by mol relative to the total exchange capacity of the cation exchange resin.

In addition, the polyvalent amine may be at least one selected from the group consisting of hydrazine, ethylenediamine, diethylenetriamine, triethylenetetramine and 1,3-propanediamine.

Then, the aldehyde may be at least one selected from the group consisting of acetaldehyde, propionaldehyde, butyl-aldehyde and condensates thereof.

In addition, the carboxylic acid may be acetic acid. The cation exchange resin is preferably a strongly acidic cation-exchange resin.

The method for removing aldehyde of the present invention is a method for bringing a carboxylic acid-containing liquid containing aldehyde into contact with the aldehyde adsorbent to thereby adsorb and remove aldehyde.

Then, the carboxylic acid-containing liquid containing aldehyde may be, for example, an acetic acid-containing liquid produced during production of acetic acid by carbonylation of methanol, wherein the acetic acid-containing liquid may be at least one of process liquids produced during this production and absorption liquids in which low boiling components included in process gases produced during this production is absorbed.

The method for producing acetic acid of the present invention is a method for producing acetic acid, including a carbonylation reaction step of carbonylating methanol by carbon monoxide to produce acetic acid, a flash evaporation step of evaporating a part of a reaction product liquid produced in the carbonylation reaction step to separate the reaction product liquid to vapor and liquid phases, a light ends distillation step of distilling the vapor phase produced in the flash evaporation step to yield a bottom product serving as an acetic acid product, and a liquid flown out from a column top, to be circulated to the carbonylation reaction step, and an aldehyde adsorption step of bringing, into contact with the aldehyde adsorbent, at least one of process liquids produced in steps of the carbonylation reaction step, the flash evaporation step and the light ends distillation step, and absorption liquids in which low boiling components included in process gases produced in these steps is absorbed.

Then, the method may further include a separation step of separating the liquid flown out from the column top, produced in the light ends distillation step, to aqueous and oil phases, and a circulation step of circulating the aqueous phase or the oil phase separated in the separation step to the carbonylation reaction step, wherein the process liquid may be the aqueous phase or the oil phase separated in the separation step.

In addition, the method may further include a methyl iodide recovery step of bringing an offgas produced in the carbonylation reaction step into contact with methanol to absorb methyl iodide, wherein the process liquid may be a methanol-containing liquid obtained in the methyl iodide recovery step.

In addition, the method may further include a bottom product purification step of purifying the bottom product produced in the light ends distillation step, wherein the process liquid may be at least one of the bottom product and the acetic acid product obtained in the bottom product purification step.

Then, the process liquid or the absorption liquid may be an aqueous solution including methyl iodide, methyl acetate, methanol, acetaldehyde and acetic acid.

The method for regenerating an aldehyde adsorbent of the present invention is a method for regenerating an aldehyde adsorbent, including contacting the aldehyde adsorbent, to which aldehyde is adsorbed, with an aqueous inorganic acid solution to thereby remove aldehyde together with the polyvalent amine.

Advantageous Effects of Invention

The aldehyde adsorbent including a cation exchange resin ion-exchanged with a polyvalent amine in 1 to 99% by mol of the total exchange capacity, of the present invention, can be used to thereby selectively adsorb and remove aldehyde included in a carboxylic acid-containing liquid. Accordingly, the condensation of aldehyde can be suppressed and the blockage due to aldehyde precipitated can be avoided. Then, aldehyde can be selectively removed from a carboxylic acid-containing liquid easily by an inexpensive method with no complicated and expensive apparatus. In addition, low boiling components useful for the carbonylation reaction of methanol, such as methyl iodide and methyl acetate, are also inhibited from being lost. Furthermore, the load upon purification of an acetic acid product can be reduced to achieve the stabilization of the quality of acetic acid. In addition, the aldehyde adsorbent of the present invention can include a cation exchange resin replaced with a polyvalent amine in only a part of the total exchange capacity to allow an amine group to coexist with an acid point, thereby adsorbing aldehyde at a high efficiency.

DESCRIPTION OF EMBODIMENTS

Figure 1:
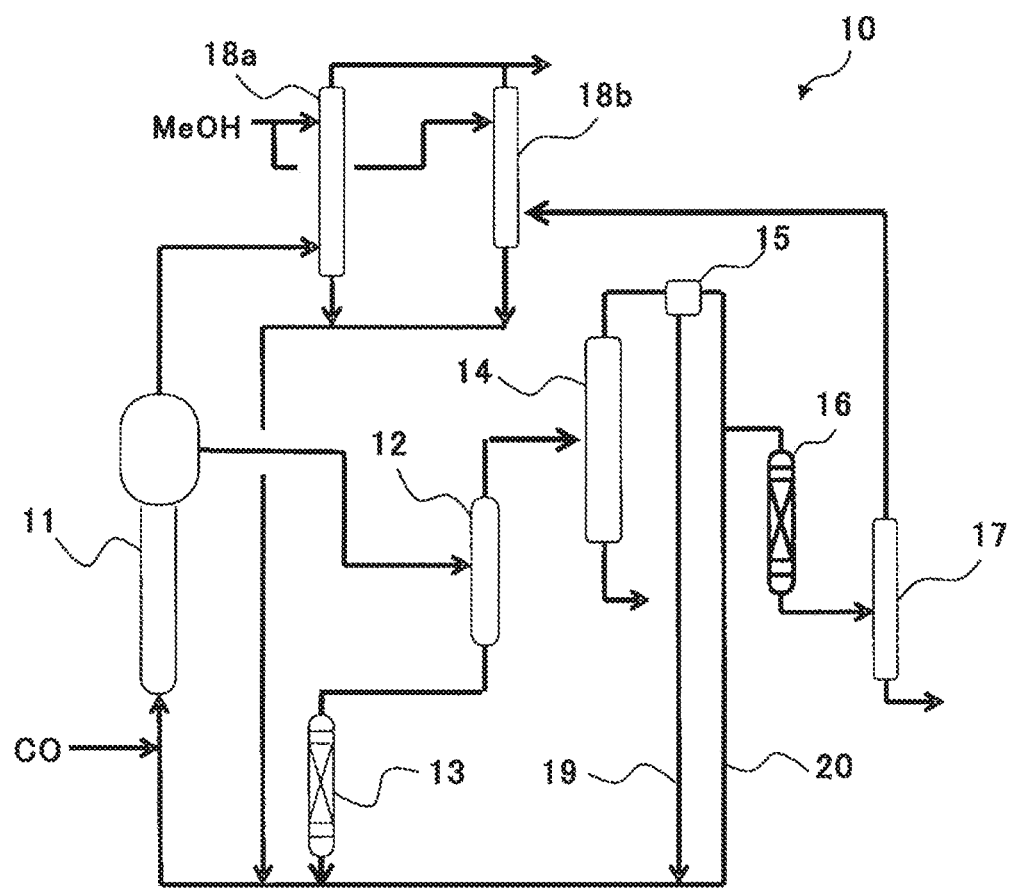
FIG. 1 is a schematic diagram illustrating one example of an acetic acid production apparatus to which the method for producing acetic acid of the present invention can be applied.

The aldehyde adsorbent for adsorbing aldehyde in a carboxylic acid-containing liquid containing aldehyde, of the present invention, includes a cation exchange resin ion-exchanged with a polyvalent amine in 1 to 99% by mol of the total exchange capacity.

The cation exchange resin is preferably a strongly acidic cation-exchange resin. The exchange group of the strongly acidic cation-exchange resin includes a sulfo group ($-SO_3H$). Specific examples include Amberlyst 15 (produced by The Dow Chemical Company), Diaion (produced by Mitsubishi Chemical Corporation), DOWEX (produced by The Dow Chemical Company) and CT175 (produced by Purolite K. K.). In addition, the type of the cation exchange resin is not particularly limited, and any cation exchange resin of a porous type having macropores (including all of porous, high porous and MR types) and a gel type having no macropores can be used.

The polyvalent amine includes diamine, triamine and tetramine, and specific examples include hydrazine, ethylenediamine, diethylenetriamine, triethylenetetramine and 1,3-propanediamine.

In the present invention, the amount ion-exchanged with the polyvalent amine corresponds to 1 to 99% by mol of the total exchange capacity of the cation exchange resin. That is, the aldehyde adsorbent of the present invention is obtained by ion-exchanging a part of the total exchange capacity of the cation exchange resin with the polyvalent amine. The amount ion-exchanged with the polyvalent amine is in practice preferably 10 to 90% by mol and further preferably 40 to 80% by mol of the total exchange capacity of the cation exchange resin.

The method for ion-exchanging the cation exchange resin with the polyvalent amine in 1 to 99% by mol of the total exchange capacity of the resin is not particularly limited, but examples include a method for circulating, to a column filled with the cation exchange resin, an aqueous solution including the polyvalent amine in an amount corresponding to the desired amount ion-exchanged, namely, the polyvalent amine in an amount corresponding to 1 to 99% by mol of the total exchange capacity of the cation exchange resin, and a method including adding the cation exchange resin to an aqueous solution including the polyvalent amine in an amount corresponding to the desired amount ion-exchanged, and shaking the resultant.

Such an aldehyde adsorbent including the cation exchange resin ion-exchanged with the polyvalent amine in 1 to 99% by mol of the total exchange capacity can be brought into contact with a carboxylic acid-containing liquid containing aldehyde to thereby selectively adsorb aldehyde in the carboxylic acid-containing liquid containing aldehyde, removing aldehyde contained in the carboxylic acid-containing liquid. Accordingly, the condensation of aldehyde in the system can be suppressed, and the blockage of an apparatus such as a column due to aldehyde precipitated can be avoided. Then, since the present invention is directed to the removal by an adsorbent including a cation exchange resin on which a polyvalent amine is supported, aldehyde can be removed from a carboxylic acid-containing liquid easily by an inexpensive method with no complicated and expensive apparatus, unlike to the case in PTL 1. In addition, the following problem as in PTL 2 is also solved: low boiling components useful, for example, for the carbonylation reaction of methanol, such as methyl iodide and methyl acetate, are removed. Then, when the present invention is applied to, for example, a method for producing acetic acid, the load upon purification of an acetic acid product can be reduced to achieve the stabilization of the quality of the acetic acid product. Although the detail is described later, the aldehyde adsorbent of the present invention can include a cation exchange resin replaced with a polyvalent amine in only a part of the ion exchange capacity to allow an amine group to coexist with an acid point, thereby adsorbing aldehyde at a high efficiency.

The aldehyde includes aliphatic aldehydes such as acetaldehyde, propionaldehyde and butylaldehyde, and condensates thereof such as crotonaldehyde and paraldehyde.

The carboxylic acid includes acetic acid and propionic acid.

The method for bringing the aldehyde adsorbent into contact with the carboxylic acid-containing liquid containing aldehyde is not particularly limited, but examples include a flowing method including feeding the carboxylic acid-containing liquid containing aldehyde to a column filled with the aldehyde adsorbent in an upflow manner or a downflow manner, a method including allowing the aldehyde adsorbent to be formed into a fluid bed in the state of being suspended in the carboxylic acid-containing liquid containing aldehyde, and a method including bringing the carboxylic acid-containing liquid containing aldehyde into contact with the aldehyde adsorbent and shaking the resultant. The contact temperature is not particularly limited, but the aldehyde adsorbent is preferably brought into contact with the carboxylic acid-containing liquid containing aldehyde at 100° C. or lower. In addition, the amount of the aldehyde adsorbent is not particularly limited, and may be determined based on the amount of aldehyde contained in the carboxylic acid-containing liquid containing aldehyde, the adsorption capacity of the aldehyde adsorbent, and the like. The adsorption to be performed by bringing the aldehyde adsorbent into contact with the carboxylic acid-containing liquid containing aldehyde may be, of course, continuously or intermittently performed.

The mechanism where the aldehyde adsorbent including the cation exchange resin ion-exchanged with the polyvalent amine in 1 to 99% by mol of the total exchange capacity, of the present invention, can thus remove aldehyde contained in the carboxylic acid-containing liquid at a high efficiency is presumed as follows.

First, a part of the cation exchange resin is ion-exchanged with the polyvalent amine to thereby bind one amino group of the polyvalent amine to the cation exchange resin, allowing the polyvalent amine to be supported on the cation exchange resin. An amino group not bound to the cation exchange resin, included in the polyvalent amine bound to the cation exchange resin, can be bound to aldehyde by a nucleophilic addition reaction. In the present invention, since the amount ion-exchanged with the polyvalent amine is 1 to 99% by mol of the total exchange capacity of the cation exchange resin, the acid point of the cation exchange resin, namely, $H^+$ of a sulfo group or the like remains even after ion-exchange with the polyvalent amine.

Then, the carboxylic acid-containing liquid containing aldehyde is brought into contact with the cation exchange resin partially ion-exchanged with the polyvalent amine. Herein, an amino group not bound to the cation exchange resin, of the polyvalent amine supported on the cation exchange resin, is protected by the acid point remaining in the cation exchange resin to prevent the amino group not bound to the cation exchange resin and carboxylic acid from being in contact with each other. Accordingly, the amino group not bound to the cation exchange resin is subjected to a selective nucleophilic addition reaction with aldehyde to allow aldehyde to be selectively adsorbed to the cation exchange resin and removed.

In addition, since the acid point remaining in the cation exchange resin not only prevents carboxylic acid and the amino group from being brought in contact with each other but also serves as a catalyst for the condensation reaction of aldehyde bound to the amino group with unreacted aldehyde, a multimer of aldehyde can be formed. For example, in the case of acetaldehyde, the condensation can progress until a trimer, paraldehyde, is obtained $(3CH_3CHO \rightarrow C_6H_{12}O_3)$.

A part of the acid point of the cation exchange resin thus remains to enable to bind the multimer, aldehyde, to the polyvalent amine with which the cation exchange resin is ion-exchanged, adsorbing aldehyde in an amount of several molar times that of the polyvalent amine supported on the cation exchange resin (in an amount of 3 molar times in the case of the acetaldehyde). Accordingly, the aldehyde adsorbent of the present invention can remove aldehyde contained in the carboxylic acid-containing liquid at a high efficiency.

On the other hand, when the cation exchange resin is replaced with the polyvalent amine in the entire of the total exchange capacity, the effect of protecting an amino group by the acid point of the cation exchange resin and the catalyst effect are not achieved, and thus the removal efficiency of aldehyde is low as compared with that of the present invention. In addition, when the cation exchange resin is not ion-exchanged with the polyvalent amine, aldehyde cannot be removed.

PTL 3 describes that carboxylic acids that react with an amino group are also removed together with aldehyde. In the present invention, however, a part of the cation exchange resin is ion-exchanged with the polyvalent amine as described above and thus the acid point of the cation exchange resin remains, thereby resulting in the effect of protecting an amino group. In addition, since the carboxylic acid-containing liquid usually includes water, the neutralization reaction of carboxylic acid with an amino group hardly progresses thermodynamically. Accordingly, in the present invention, the influence of carboxylic acid on the removal of aldehyde can be eliminated and aldehyde can be selectively removed from the carboxylic acid-containing liquid.

Herein, the amount of aldehyde that can be removed by the aldehyde adsorbent of the present invention is determined by a relationship between the amount of the polyvalent amine supported on the cation exchange resin (namely, amount ion-exchanged) and the amount of the acid point remaining in the cation exchange resin, and thus is not increased when the amount ion-exchanged relative to the total exchange capacity of the cation exchange resin is a certain value or more.

The aldehyde adsorbent of the present invention can be regenerated by the same method as that of a usual cation exchange resin. Specifically, the aldehyde adsorbent of the present invention can be washed with an aqueous inorganic acid solution such as sulfuric acid and hydrochloric acid (i.e. the aldehyde adsorbent of the present invention can be contacted with an aqueous inorganic acid solution such as sulfuric acid and hydrochloric acid) to thereby remove aldehyde together with the polyvalent amine. Examples of the method for contacting the aldehyde adsorbent with an aqueous inorganic acid solution include a method including feeding an aqueous inorganic acid solution such as sulfuric acid and hydrochloric acid in a concentration of 0.1 to 2.0 mol/L, desirably in a concentration of about 0.5 mol/L to a column filled with the aldehyde adsorbent, and a method including adding the aldehyde adsorbent to the aqueous inorganic acid solution and shaking the resultant.

When the aldehyde adsorbent of the present invention is contacted with the aqueous inorganic acid solution, the polyvalent amine bound to the multimer aldehyde is desorbed from the cation exchange resin by the ion-exchange action of a proton. A part of the cation exchange resin contacted with the aqueous inorganic acid solution can be replaced with the polyvalent amine again and thus used for the selective removal of aldehyde from the carboxylic acid-containing liquid. In the present invention, since the multimer of aldehyde is desorbed by the acid together with the polyvalent amine supported on the cation exchange resin as described above, a larger amount of aldehyde can be desorbed from the cation exchange resin by a smaller amount of the acid. Accordingly, the amount of the acid for use in regenerating can be smaller.

Such a method for removing aldehyde from the carboxylic acid-containing liquid containing aldehyde by using the aldehyde adsorbent of the present invention can be applied to a method for producing acetic acid. That is, to a conventional method for producing acetic acid (for example, a method for producing acetic acid, including carbonylating methanol by carbon monoxide to produce acetic acid and purifying the acetic acid by distillation or the like, and circulating low boiling components of a process liquid and a process gas produced) can be added an aldehyde adsorption step of bringing, into contact with the aldehyde adsorbent of the present invention, a process liquid produced in the production of acetic acid and an absorption liquid in which low boiling components of a process gas are absorbed. For example, the method for producing acetic acid of the present invention includes a carbonylation reaction step of carbonylating methanol by carbon monoxide to produce acetic acid, a flash evaporation step of evaporating a part of a reaction product liquid produced in the carbonylation reaction step to separate the reaction product liquid to vapor and liquid phases, a light ends distillation step of distilling the vapor phase produced in the flash evaporation step to yield a bottom product serving as an acetic acid product and a liquid flown out from the column top, to be circulated to the carbonylation reaction step, and an aldehyde adsorption step of bringing, into contact with the aldehyde adsorbent of the present invention, at least one of process liquids produced in steps of the carbonylation reaction step, the flash evaporation step and the light ends distillation step, and absorption liquids in which low boiling components included in process gases produced in these steps are absorbed.

First, methanol is carbonylated by carbon monoxide to produce acetic acid (carbonylation reaction step). The method for reacting methanol with carbon monoxide to produce acetic acid is not particularly limited, but may be, for example, a heterogeneous system in which methanol is reacted with carbon monoxide in a liquid phase including a solid catalyst having a complex of rhodium, iridium or the like supported and a co-catalyst such as methyl iodide. The method may also be a homogeneous system in which a noble metal catalyst dissolved in a liquid phase, such as rhodium and iridium, is used instead of the solid catalyst.

The solid catalyst includes a solid catalyst having a noble metal complex supported on a resin carrier containing quaternized nitrogen. The resin carrier containing quaternized nitrogen is typically a pyridine resin, namely, a resin including in its structure a pyridine ring whose nitrogen atom can be quaternized, and representatively, for example, a copolymer of 4-vinylpyridine and divinylbenzene. The resin carrier, however, is not limited to this particular resin, and is meant to comprehensively include a resin containing basic nitrogen that can be quaternized to adsorb and support the noble metal complex. Accordingly, it is possible to use a resin including instead of the 4-vinylpyridine 2-vinylpyridine having a vinyl group at a different position, substituted vinylpyridines such as vinylmethylpyridine or various basic nitrogen-containing monomers such as vinylquinolines, or to use a resin including instead of divinylbenzene various crosslinkable monomers having two or more groups including an ethylenically unsaturated bond. Furthermore, it is also possible to use a resin including other polymerizable comonomer such as styrene and methyl acrylate in addition to the basic nitrogen-containing monomer and the crosslinkable monomer.

The noble metal complex supported on the resin carrier refers to a complex of a noble metal that exhibits a catalytic action to the carbonylation reaction, the complex being adsorbed to the quaternized nitrogen of the resin carrier in an ion-exchange manner. As such a noble metal, rhodium or iridium is known, and in general rhodium is suitably used. When the resin carrier is brought into contact with a halide of rhodium or a rhodium salt such as rhodium acetate in a solution including methyl iodide under carbon monoxide pressure (0.7 to 3 MPa), rhodium can be supported on the resin carrier. Herein, a nitrogen atom in the resin carrier is quaternized, and a rhodium complex ion produced by a reaction of rhodium, methyl iodide and carbon monoxide, namely, a rhodium carbonyl iodide complex $[Rh(CO)_2I_2]^-$ is bound thereto in an ion-exchange manner, providing a solid catalyst.

A reactor filled with the solid catalyst or the metal catalyst is filled with a mixed liquid including methanol as a reaction raw material, a reaction solvent and a co-catalyst as a reaction liquid. As the reaction solvent, various conventionally known solvents are used. While this reaction is usually performed using acetic acid as the reaction solvent, acetic acid is a reaction product and at the same time serves as the reaction solvent in this case. Since this reaction produces methyl acetate, dimethyl ether, water, acetaldehyde and the like as by-products, and these by-products are returned together with the solvent, the reaction promoter and the unreacted raw material to the carbonylation reaction step as the residual liquid from which acetic acid is separated and recovered as a product, the liquid phase in the carbonylation reaction step includes a mixture of all these components. The carbonylation reaction step can be performed using various types of reactors such as a fixed bed, an expanded bed and a mixing tank, and any of a batch type operation and a continuous type operation may be adopted therefor, but a continuous type mixing tank in which reaction conditions are easily controlled is industrially preferable.

Then, the reaction product liquid from the carbonylation reaction step (having the same composition as the liquid phase in the carbonylation reaction step in the case of the continuous type mixing tank) is first partially evaporated in a flash evaporation portion and separated to a vapor phase and a liquid phase (flash evaporation step), and thereafter the vapor phase is guided to a light ends distillation column and acetic acid serving as an acetic acid product is separated as a bottom product from the lower portion of the light ends distillation column (light ends distillation step). The residual liquid other than acetic acid separated and recovered, such as the bottom product obtained in the flash evaporation portion and the liquid flown out from the column top obtained in the light ends distillation step, while a part thereof is purged from the process, appropriately undergoes the purification step to be returned to the carbonylation reaction step.

The reason why the light ends distillation step is thus carried out following the flash evaporation step is because, while the reaction product liquid is a mixture of various components as described above and acetic acid is a component having a small volatility among them, a lower-volatile (or non-volatile) impurity is actually incorporated to acetic acid and thus acetic acid may not be recovered from the bottom product of the flash evaporation portion as a product. Herein, the flash evaporation step and the light ends distillation step can be carried out as a series of steps or as separate steps. That is, for example, the flash evaporation portion and the light ends distillation column can be integrally provided on the bottom portion and the upper portion of a single column, or can be separated to a flasher and the light ends distillation column to be each configured as a different column.

Then, in the present invention, the process liquid (liquid) produced in the production of acetic acid, specifically, the process liquid (namely, the reaction product liquid produced in the carbonylation reaction) produced in the carbonylation reaction step, the process liquid produced in the flash evaporation step and the process liquid produced in the light ends distillation step are brought into contact with the aldehyde adsorbent of the present invention (aldehyde adsorption step). The absorption liquid in which low boiling components included in the process gas (gas) produced in the production of acetic acid, specifically, the process gas (namely, an offgas produced in the carbonylation reaction) produced in the carbonylation reaction step, the process gas produced in the flash evaporation step and the process gas produced in the light ends distillation step are absorbed to water, methanol, acetic acid or the like may also be brought into contact with the aldehyde adsorbent of the present invention. Herein, the low boiling components are components evaporated in the production step of acetic acid, among components included in the process gas. The low boiling components include methyl iodide, methyl acetate, acetic acid and aldehyde.

Since acetaldehyde is by-produced in the production of acetic acid by the carbonylation of methanol as described above, the process liquids and the process gases obtained in the carbonylation reaction step, the flash evaporation step and the light ends distillation step include acetaldehyde. Herein, the process liquids and the process gases also include components such as water, acetic acid, methyl iodide, methyl acetate and methanol, in addition to acetaldehyde.

When acetaldehyde is present in the system in which the production of acetic acid is carried out, it causes a condensation reaction under the carbonylation condition to be converted into unsaturated aldehydes having a high boiling point. These unsaturated aldehydes are precipitated in the lower portion of the distillation column or the like to cause the problem of blockage or the like, along with further progress of the condensation. In addition, crotonaldehyde or the like has a boiling point close to that of acetic acid, and thus is difficult to be separated in the purification step of acetic acid and is incorporated into an acetic acid product, resulting in the deterioration in quality of acetic acid particularly as a reducing substance. In particular, when the low boiling components included in the process liquids and the process gases produced in the respective steps are circulated to the reaction system of acetic acid in order to recover and reuse the low boiling components as components useful for the carbonylation reaction of methanol, such as methyl acetate and methyl iodide, acetaldehyde is accumulated.

Since acetaldehyde can be suitably adsorbed by the aldehyde adsorbent and removed in the aldehyde adsorption step in the method for producing acetic acid of the present invention, the problem of aldehyde being precipitated to cause blockage in a production apparatus such as the lower portion of a distillation column can be solved. In addition, the bottom product produced in the light ends distillation step can be subjected to the aldehyde adsorption step to thereby provide a high quality acetic acid product.

The aldehyde adsorption step may bring the process liquids produced in the carbonylation reaction step, the flash evaporation step and the light ends distillation step, and the absorption liquid in which low boiling components included in the process gases produced in these steps are absorbed to water, methanol, acetic acid or the like into contact with the aldehyde adsorbent of the present invention in the same method as in the case of the carboxylic acid-containing liquid containing aldehyde. The contacting manner is not particularly limited, and can be performed by at least one or a combination of a continuous flow type and a batch type. When the continuous flow type is herein used, the direction in which the process liquids and the absorption liquid are flown to the column filled with a predetermined cation exchange resin may be an upflow or downflow direction.

The method for producing acetic acid of the present invention may also further include a separation step of separating the liquid flown out from the column top, produced in the light ends distillation step, to an aqueous phase and an oil phase, and a circulation step of circulating the aqueous phase or the oil phase separated in the separation step to the carbonylation reaction step. Then, the aqueous phase or the oil phase separated in the separation step may be used as a process liquid that is a liquid to be treated in the aldehyde adsorption step. That is, the aldehyde adsorption step may also be carried out in the subsequent step of the separation step.

A part or all of the aqueous phase or the oil phase separated in the separation step may be subjected to the aldehyde adsorption step. For example, only a part of the aqueous phase separated in the separation step may be circulated to the carbonylation reaction step via the aldehyde adsorption step.

The separation step includes a method in which the liquid flown out from the column top is left to still stand in a container to thereby be separated to an aqueous phase and an oil phase. In addition, the circulation step can be carried out, for example, by a liquid-feeding unit for returning the oil phase or the aqueous phase from a container for carrying out the separation step to the carbonylation reaction step, such as a pipe and a pump.

The method of the present invention may further include an excess water removal step of removing excess water by-produced in the carbonylation reaction step, after the aqueous phase separated in the separation step is if necessary brought into contact with the aldehyde adsorbent in the aldehyde adsorption step. The method for removing excess water is, for example, distillation. In the excess water removal step, useful components such as methyl iodide and methyl acetate are recovered to the oil phase. Then, an aqueous phase obtained in the excess water removal step can be discharged outside of the system.

The method of the present invention may also further include a methyl iodide recovery step of bringing an offgas produced in the carbonylation reaction step into contact with methanol to recover methyl iodide, wherein a methanol-containing liquid obtained in the methyl iodide recovery step may serve as the liquid to be treated in the aldehyde adsorption step. That is, the aldehyde adsorption step may also be carried out in the subsequent step of the methyl iodide recovery step.

The offgas produced in the carbonylation reaction step is, for example, a gas including unreacted carbon monoxide, methanol, methyl iodide, methyl acetate, acetic acid, acetaldehyde and the like discharged from the top portion of the reactor for carrying out the carbonylation reaction step. In the methyl iodide recovery step, this offgas is brought into contact with methanol to absorb useful components such as methyl iodide and also methyl acetate in the offgas. For example, the offgas may be introduced from the lower portion of a methyl iodide absorption column to be brought into contact with liquid methanol that is allowed to drop from the upper portion. The methanol-containing liquid absorbing methyl iodide and the like may be appropriately circulated to the carbonylation reaction step via the aldehyde adsorption step. In addition, the offgas which is discharged from, for example, the top portion of the methyl iodide absorption column and methyl iodide is removed is discharged outside of the reaction system after being if necessary purified by activated carbon or the like.

The method of the present invention may also further include a step of bringing a process gas including methyl iodide, methyl acetate and the like produced in the excess water removal step into contact with methanol to recover methyl iodide. This methyl iodide recovery step may be carried out by the same method as in the methyl iodide recovery step. Then, a methanol-containing liquid obtained in this methyl iodide recovery step may also serve as the liquid to be treated in the aldehyde adsorption step. The methanol-containing liquid absorbing methyl iodide may be appropriately circulated to the carbonylation reaction step via the aldehyde adsorption step.

The method of the present invention may also further include a bottom product purification step of purifying the bottom product produced in the light ends distillation step and serving as an acetic acid product. Then, the bottom product produced in the light ends distillation step and serving as an acetic acid product, or an acetic acid product obtained in the bottom product purification step may serve as the liquid to be treated in the aldehyde adsorption step. That is, the aldehyde adsorption step may also be carried out in the subsequent step of the light ends distillation step or the bottom product purification step.

The bottom product purification step may perform, for example, such purification that the bottom product produced in the light ends distillation step is distilled in a distillation column for acetic acid purification to allow a component having a higher molecular weight than acetic acid, such as propionic acid, to be removed.

The method of the present invention may also include a step (basic nitrogen compound removal step) of bringing the liquid phase of the flash evaporation portion into contact with an acidic cation-exchange resin on the way of the route in which the liquid phase of the flash evaporation portion is returned to the carbonylation reaction step, thereby removing a basic nitrogen-containing compound produced by thermal decomposition of a pyridine resin carrier or the like.

The liquid phase of the flash evaporation portion mainly includes acetic acid, but if basic nitrogen-containing molecules such as a pyridine ring are eluted by decomposition of the resin carrier of the solid catalyst, these molecules are also included in the liquid phase of the flash evaporation portion. When the liquid phase including such basic nitrogen-containing molecules (which are quaternized) is returned to the carbonylation reaction step as it is, such molecules are accumulated in the liquid phase in the carbonylation reaction step, and cause such distribution that basic nitrogen-containing sites in the resin carrier of the solid catalyst and the ion of the noble metal complex are lost. That is, the noble metal complex is free in the liquid phase in the carbonylation reaction step in a larger amount to result in the deterioration in catalyst function. The basic nitrogen compound removal step can be carried out to thereby suppress the deterioration in catalyst function.

An acetic acid production apparatus to which such a method for producing acetic acid of the present invention can be applied is described with reference to FIG. 1. FIG. 1 is a schematic diagram illustrating one example of an acetic acid production apparatus to which the method for producing acetic acid of the present invention can be applied.

As illustrated in FIG. 1, an acetic acid production apparatus 10 includes a carbonylation reactor 11 for carbonylating methanol by carbon monoxide to produce acetic acid, a flasher 12 that is a flash evaporation unit for evaporating a part of a reaction product liquid discharged from the carbonylation reactor 11 to separate the reaction product liquid to vapor and liquid phases, a light ends distillation column 14 that is a light ends distillation unit for distilling the vapor phase discharged from the flasher 12 to produce a bottom product serving as an acetic acid product and a liquid flown out from the column top, and a decanter 15 that is a separation unit for separating the liquid flown out from the column top produced in the light ends distillation column 14 to an aqueous phase and an oil phase, wherein the oil phase discharged from the decanter 15 is returned via a pipe 19 to the carbonylation reactor 11 together with a liquid of the aqueous phase sent from the decanter 15 via a pipe 20.

The acetic acid production apparatus 10 illustrated in FIG. 1 also includes a basic nitrogen compound adsorption column 13 for bringing the liquid phase discharged from the flasher 12 into contact with an acidic cation-exchange resin.

Then, as illustrated in FIG. 1, an aldehyde adsorption column 16 for bringing a part of the aqueous phase discharged from the decanter 15 into contact with the aldehyde adsorbent of the present invention is provided on a pipe bifurcated from the pipe 20 in the subsequent step of the decanter 15. The aldehyde adsorption column 16 is a column filled with the aldehyde adsorbent of the present invention.

While a subject to be treated of the aldehyde adsorbent of the present invention is the aqueous phase discharged from the decanter 15 in FIG. 1, the subject to be treated may be a process liquid produced in other step or an absorption liquid in which low boiling components included in a process gas produced therein are absorbed, wherein the aldehyde adsorption column 16 may be provided on the subsequent step of the step in which the process liquid or the process gas serving as the subject to be treated is produced.

The acetic acid production apparatus 10 illustrated in FIG. 1 is also provided with an excess water distillation column 17 in the subsequent step of the aldehyde adsorption column 16, for distilling the aqueous phase discharged from the aldehyde adsorption column 16 to remove excess water by-produced in the carbonylation reaction step and to separate methyl iodide, methyl acetate and the like.

The acetic acid production apparatus 10 illustrated in FIG. 1 is further provided with a methyl iodide absorption column 18a for allowing an offgas that is a gas including carbon monoxide, methanol vapor, methyl iodide and methyl acetate discharged from the top portion of the carbonylation reactor 11 to be introduced thereto to bring the offgas into contact with methanol for recovery of methyl iodide and the like. The methyl iodide absorption column 18a is configured so as to allow the offgas to be introduced thereto from the lower portion thereof and so as to allow liquid methanol to drop from the upper portion thereof.

The acetic acid production apparatus 10 illustrated in FIG. 1 is also provided with a methyl iodide absorption column 18b for allowing a gas including methyl iodide and methyl acetate discharged from the top portion of the excess water distillation column 17 to be introduced thereto to bring the gas into contact with methanol for recovery of methyl iodide. The methyl iodide absorption column 18b is also configured so as to allow the gas to be introduced thereto from the lower portion thereof and so as to allow liquid methanol to drop from the upper portion thereof, as in the methyl iodide absorption column 18a. The methyl iodide absorption column 18b, however, is operated at a lower pressure than that in the methyl iodide absorption column 18a.

The method for producing acetic acid using such an acetic acid production apparatus 10 is exemplified below. First, methanol and carbon monoxide are introduced to the carbonylation reactor 11, and reacted with each other to produce acetic acid. The detail is as follows: a solid catalyst is present with being dispersed in a liquid phase in the carbonylation reactor 11; the liquid phase includes acetic acid as a solvent, methyl iodide as a reaction promoter, methanol as a reaction raw material, and various reaction by-products (methyl acetate, acetaldehyde, water and the like); carbon monoxide gas is blown into the reaction liquid, in which the solid catalyst is dispersed, to react methanol with carbon monoxide under conditions of, for example, a reaction temperature of about 100 to 200° C. and a reaction pressure of about 1 to 5 MPa, producing acetic acid.

The offgas discharged from the top portion of the carbonylation reactor 11 is introduced to the methyl iodide absorption column 18a from the lower portion. The offgas introduced to the methyl iodide absorption column 18a is brought into contact with liquid methanol allowed to drop from the upper portion of the methyl iodide absorption column 18a, and methyl iodide is absorbed to liquid methanol. A methanol-containing liquid absorbing methyl iodide and the like is returned to the carbonylation reactor 11. In addition, the offgas which is discharged, for example, from the top portion of the methyl iodide absorption column 18a and methyl iodide and the like are removed is discharged outside of the reaction system.

On the other hand, the reaction product liquid of the carbonylation reactor 11 is taken out through a screen or the like and introduced to the flasher 12. Then, the reaction product liquid is partially evaporated by flash evaporation to be formed into a vapor phase and a liquid phase.

The liquid phase produced by flash evaporation is flown to the basic nitrogen compound adsorption column 13, the basic nitrogen compound is adsorbed and removed, and thereafter the resultant is returned to the carbonylation reactor 11.

In addition, the vapor phase produced by flash evaporation is flown to the subsequent step, the light ends distillation column 14. In the light ends distillation column 14, while the vapor phase flown into from the flasher 12 is separated by distillation, a part of acetic acid having the smallest volatility among components forming the vapor phase flown into from the flasher 12 can be included in a column top distillate to allow all other vapor phase components to be included in the column top distillate. Most of acetic acid included in the vapor phase in the flasher 12 is taken out as a bottom product from the lower portion of the light ends distillation column 14, appropriately subjected to a purification treatment, and then separated and recovered as a product.

On the other hand, the liquid flown out from the column top of the light ends distillation column 14 is introduced to the decanter 15, and separated to an aqueous phase and an oil phase. The oil phase of the decanter 15 is returned via the pipe 19 to the carbonylation reactor 11 with being mixed with a liquid of the aqueous phase sent from the decanter 15 via a pipe 20.

Then, a part of the aqueous phase of the decanter 15 is bifurcated from the pipe 20 and fed to the aldehyde adsorption column 16 filled with the aldehyde adsorbent of the present invention, and aldehyde is removed therefrom.

Thereafter, the aqueous phase from which aldehyde is removed is sent to the excess water distillation column 17 and distilled. The aqueous phase discharged from the excess water distillation column 17 is discharged outside of the reaction system. On the other hand, the gas including methyl iodide, methyl acetate and the like discharged from the top portion of the excess water distillation column 17 is introduced to the methyl iodide absorption column 18b from the lower portion. The gas introduced to the methyl iodide absorption column 18b is brought into contact with liquid methanol allowed to drop from the upper portion of the methyl iodide absorption column 18b, and methyl iodide is absorbed to liquid methanol. The methanol-containing liquid absorbing methyl iodide and the like is returned to the carbonylation reactor 11. In addition, the offgas discharged from, for example, the top portion of the methyl iodide absorption column 18b, from which methyl iodide and the like are removed, is discharged outside of the reaction system.

EXAMPLES

Hereinafter, the present invention is described with reference to Examples for further understanding of the present invention, but is not limited to Examples at all.

Examples 1 to 7 and Comparative Example 1

An amount listed in the column "Amount of Amberlyst-15 added (g)-dry" in Table 1 of Amberlyst 15 (produced by The Dow Chemical Company, total exchange capacity: 5.38 mmol/g-dry, water content: 54.0% by weight), 200 ml of ion-exchange water, and an amount listed in the column "Amount of hydrazine monohydrate added" in Table 1 of hydrazine monohydrate (the amount of the hydrazine corresponding to 26 to 100% by mol of the total exchange capacity of the cation exchange resin in each of Examples and Comparative Example) were placed in a 500 ml screw-top Erlenmeyer flask, and shaken and stirred at room temperature for 5 hours. Then, the supernatant was drawn by a dropper, 200 ml of ion-exchange water was added and stirred, and then the supernatant was removed again. This operation was repeated 10 times to perform replacement washing.

Figure 2:
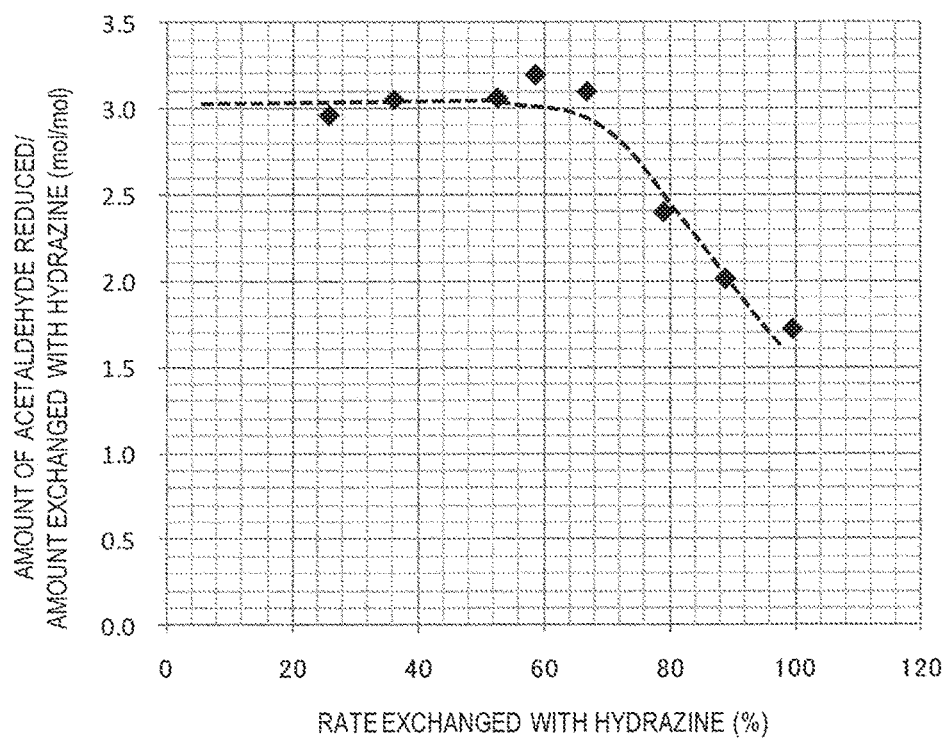
FIG. 2 is a graph showing a relationship between the rate exchanged with hydrazine and the amount of acetaldehyde reduced/the amount exchanged with hydrazine, in Examples and Comparative Example.
Figure 3:
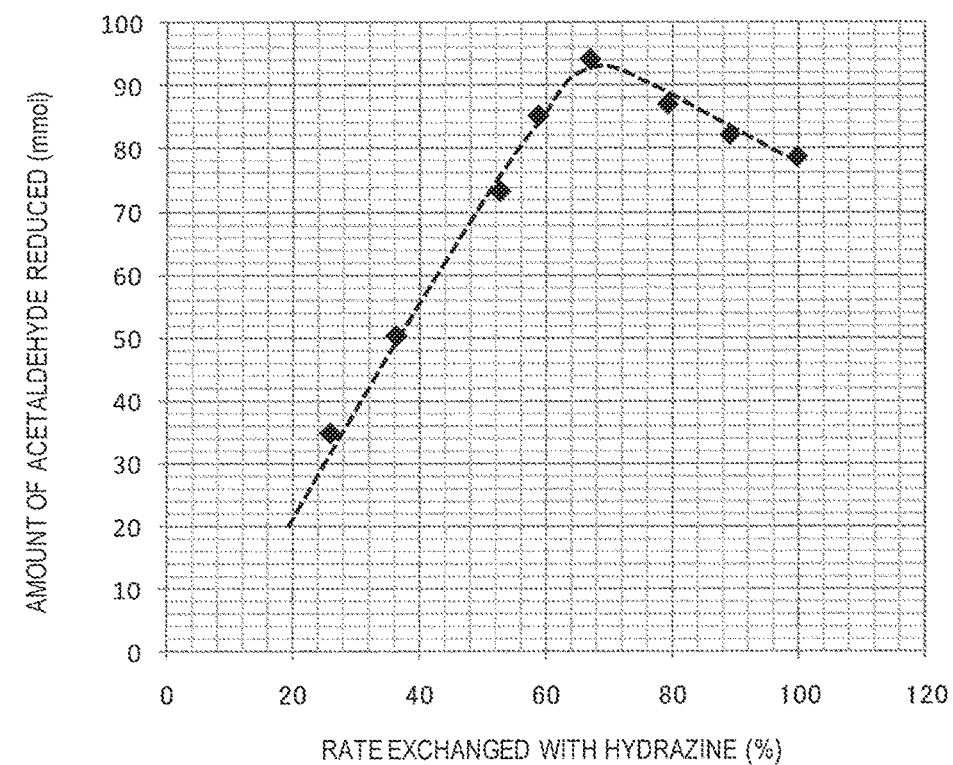
FIG. 3 is a graph showing a relationship between the rate exchanged with hydrazine and the amount of acetaldehyde reduced, in Examples and Comparative Example.

In the acetic acid production apparatus illustrated in FIG. 1, 200 g of a stimulant liquid (typical composition; acetaldehyde: 3% by weight; methyl acetate: 19% by weight; methanol: 4% by weight; methyl iodide: 2% by weight; acetic acid: 5% by weight; water: 67% by weight) of the aqueous phase (the aqueous phase of the decanter) in the liquid flown out from the top of the light ends distillation column was placed in the screw-top Erlenmeyer flask where the replacement washing had been carried out, and shaken at 40° C. for 5 hours, and thereafter the acetaldehyde concentration in the supernatant liquid was analyzed by gas chromatography (GC). The results are shown in Table 1. In addition, a relationship between the rate exchanged with hydrazine and the amount of acetaldehyde reduced/the amount exchanged with hydrazine is shown in FIG. 2, and a relationship between the rate exchanged with hydrazine and the amount of acetaldehyde reduced is shown in FIG. 3.

The total exchange capacity of the cation exchange resin in each of Examples and Comparative Example is determined by multiplying the amount of Amberlyst 15 added by the total exchange capacity value of Amberlyst 15, 5.38 mmol/g-dry. Then, the amount ion-exchanged with hydrazine relative to the total exchange capacity of the cation exchange resin (listed as "rate exchanged with hydrazine (%)" in Table 1, FIG. 2 and FIG. 3) can be determined by the expression: Amount of hydrazine added (mmol)/Total exchange capacity (mmol) of cation exchange resin in each of Examples and Comparative Example×100. Herein, the entire of hydrazine added is used for ion-exchange.

As shown in Table 1, aldehyde was favorably adsorbed and removed in each of Examples 1 to 7 in which the aldehyde adsorbent of the present invention including a cation exchange resin ion-exchanged with a polyvalent amine in 1 to 99% by mol of the total exchange capacity was used. On the other hand, in Comparative Example 1 in which a cation exchange resin ion-exchanged with a polyvalent amine in 100% of the total exchange capacity was used, aldehyde could be removed but the molar ratio (the amount of acetaldehyde reduced/the amount exchanged with hydrazine) of aldehyde that could be removed to hydrazine was low as compared with the case of each of Examples 1 to 7.

The detail is as follows. It can be seen from Table 1 and FIG. 2 that the amount of acetaldehyde adsorbed was twice or more that of hydrazine in each of Examples 1 to 7, and in particular, the amount of acetaldehyde adsorbed was about 3 times that of hydrazine in each of Examples 1 to 5 in which a cation exchange resin ion-exchanged with a polyvalent amine in about 70% or less of the total exchange capacity was used. Accordingly, it can be said that aldehyde was removed at a high efficiency in Examples 1 to 7, in particular Examples 1 to 5. It is here presumed that since the amount of acetaldehyde adsorbed was about 3 times that of hydrazine in each of Examples 1 to 5, acetaldehyde was present as a trimer to be adsorbed to hydrazine.

It can also be seen from Table 1 and FIG. 3 that when the rate exchanged with hydrazine was about 70%, the amount of acetaldehyde adsorbed and removed was maximum.

TABLE 1

|  | Example 1 | Example 2 | Example 3 | Example 4 | Example 5 | Example 6 | Example 7 | Comparative Example 1 |
|---|---|---|---|---|---|---|---|---|
| Amount of Amberlyst-15 added (g)-dry | 8.43 | 8.43 | 8.43 | 8.43 | 8.43 | 8.50 | 8.50 | 8.50 |
| Amount of hydrazine monohydrate added (g) | 0.60 | 0.84 | 1.22 | 1.36 | 1.55 | 1.85 | 2.08 | 2.33 |
| Amount of hydrazine added/Total exchange capacity (mmol/mmol) | 0.26 | 0.36 | 0.53 | 0.59 | 0.67 | 0.79 | 0.89 | 1.00 |
| Rate exchanged with hydrazine (%) | 26 | 36 | 53 | 59 | 67 | 79 | 89 | 100 |
| Amount of $CH_3CHO$ added (mmol) | 54.8 | 78.7 | 106.7 | 220.6 | 131.3 | 147.8 | 143.9 | 143.7 |
| Amount of $CH_3CHO$ reduced (mmol) | 34.8 | 50.2 | 73.1 | 85.1 | 94.1 | 87.0 | 82.1 | 78.6 |
| Rate of $CH_3CHO$ reduced (%) | 63.5 | 63.8 | 68.6 | 38.6 | 71.6 | 58.8 | 57.0 | 54.7 |
| Amount of $CH_3CHO$ reduced/Rate exchanged with hydrazine (mol/mol) | 3.0 | 3.1 | 3.1 | 3.2 | 3.1 | 2.4 | 2.0 | 1.7 |
| $CH_3CHO$(GC) (wt %) Before test | 2.41 | 3.30 | 4.20 | 8.98 | 5.63 | 6.50 | 6.33 | 3.16 |
| $CH_3CHO$(GC) (wt %) After test | 0.71 | 0.96 | 1.00 | 5.13 | 1.15 | 2.25 | 2.32 | 1.24 |

This application claims the benefit of Japanese Patent Application No. 2013-123746, filed Jun. 12, 2013, which is hereby incorporated by reference herein in its entirety.

REFERENCE SIGNS LIST

10 acetic acid production apparatus
11 carbonylation reactor
12 flasher
13 basic nitrogen compound adsorption column
14 light ends distillation column
15 decanter
16 aldehyde adsorption column
17 excess water distillation column
18a, 18b methyl iodide absorption column
19, 20 pipe

The invention claimed is:

1. An aldehyde adsorbent for adsorbing aldehyde in a carboxylic acid-containing liquid containing aldehyde, comprising a cation exchange resin ion-exchanged with a polyvalent amine in 40 to 80% by mol of the total exchange capacity of the cation exchange resin.

2. The aldehyde adsorbent according claim 1, wherein the polyvalent amine is at least one selected from the group consisting of hydrazine, ethylenediamine, diethylenetriamine, triethylenetetramine and 1,3-propanediamine.

3. The aldehyde adsorbent according to claim 1, wherein the aldehyde is at least one selected from the group consisting of acetaldehyde, propionaldehyde, butylaldehyde and condensates thereof.

4. The aldehyde adsorbent according to claim 1, wherein the carboxylic acid is acetic acid.

5. The aldehyde adsorbent according to claim 1, wherein the cation exchange resin is a strongly acidic cation-exchange resin.

6. A method for removing aldehyde, comprising bringing a carboxylic acid-containing liquid containing aldehyde into contact with the aldehyde adsorbent according to claim 1 to adsorb and remove aldehyde.

7. The method for removing aldehyde according to claim 6, wherein the carboxylic acid-containing liquid containing aldehyde is at least one of process liquids produced during production of acetic acid by carbonylation of methanol and absorption liquids in which low boiling components included in a process gas produced during the production are absorbed.

8. A method for regenerating an aldehyde adsorbent, comprising contacting the aldehyde adsorbent according to claim 1, to which aldehyde is adsorbed, with an aqueous inorganic acid solution to thereby remove aldehyde together with the polyvalent amine.

* * * * *